United States Patent
O'Keefe et al.

(10) Patent No.: US 10,238,560 B2
(45) Date of Patent: Mar. 26, 2019

(54) AIR FLUIDIZED THERAPY BED HAVING PULMONARY THERAPY

(71) Applicant: Hill-Rom Services, Inc., Batesville, IN (US)

(72) Inventors: Christopher R. O'Keefe, Columbus, OH (US); Frank E. Sauser, Cincinnati, OH (US); Kristopher A. Klink, Indianapolis, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 330 days.

(21) Appl. No.: 14/202,624

(22) Filed: Mar. 10, 2014

(65) Prior Publication Data

US 2014/0259428 A1    Sep. 18, 2014

Related U.S. Application Data

(60) Provisional application No. 61/778,789, filed on Mar. 13, 2013.

(51) Int. Cl.
*A61F 7/00* (2006.01)
*A61G 7/05* (2006.01)
(Continued)

(52) U.S. Cl.
CPC ........ *A61G 7/05761* (2013.01); *A61F 7/0097* (2013.01); *A61G 7/0514* (2016.11);
(Continued)

(58) Field of Classification Search
CPC ............ A61G 7/05761; A61G 7/05746; A61G 2007/0514; A61G 7/012; A61G 7/015; A61G 2007/0578; A61G 2203/44; A61G 2007/0528; A61G 2203/34; A61G 7/018; A61G 2007/0515; A61G 2210/90;
(Continued)

(56) References Cited

U.S. PATENT DOCUMENTS 1,772,310 A    8/1930    Hart
3,008,465 A    11/1961    Andrew
(Continued)

FOREIGN PATENT DOCUMENTS

AU    2006269277 A1    1/2007
AU    2006269277 B2    2/2012
(Continued)

OTHER PUBLICATIONS

Search Report, EP14159207.1, 9 pgs.
(Continued)

*Primary Examiner* — Robert G Santos
*Assistant Examiner* — Myles A Throop
(74) *Attorney, Agent, or Firm* — Barnes & Thornburg LLP (57) ABSTRACT

A patient support apparatus includes an air supply and an air fluidization therapy bed including a fluidization space and a fluidizable medium positioned in the fluidization space. The air fluidization therapy bed receives a flow of pressurized air from the air supply. The flow of pressurized air operable to fluidize the fluidizable medium. The patient support apparatus is configured to provide other therapies, such as pulmonary therapies, in addition to the air fluidization therapy.

20 Claims, 10 Drawing Sheets

(51) Int. Cl.
  *A61H 9/00* (2006.01)
  *A61G 7/012* (2006.01)
  *A61G 7/015* (2006.01)
  *A61G 7/018* (2006.01)
  *A61G 7/057* (2006.01)
  *A61H 23/00* (2006.01)
  *A61H 23/02* (2006.01)
  *A61H 23/04* (2006.01)
  *A61H 33/00* (2006.01)

(52) U.S. Cl.
  CPC .......... *A61G 7/0515* (2016.11); *A61G 7/0528* (2016.11); *A61G 7/05746* (2013.01); *A61G 7/05784* (2016.11); *A61H 9/005* (2013.01); *A61H 9/0071* (2013.01); *A61H 9/0078* (2013.01); *A61H 23/006* (2013.01); *A61H 23/0245* (2013.01); *A61H 23/04* (2013.01); *A61F 2007/0063* (2013.01); *A61F 2007/0091* (2013.01); *A61G 7/012* (2013.01); *A61G 7/015* (2013.01); *A61G 7/018* (2013.01); *A61G 2203/34* (2013.01); *A61G 2203/44* (2013.01); *A61G 2210/70* (2013.01); *A61G 2210/90* (2013.01); *A61H 9/0021* (2013.01); *A61H 2033/0004* (2013.01); *A61H 2201/10* (2013.01); *A61H 2201/1654* (2013.01); *A61H 2201/1697* (2013.01); *A61H 2201/5007* (2013.01); *A61H 2203/0456* (2013.01); *A61H 2205/081* (2013.01); *A61H 2205/084* (2013.01); *A61H 2205/10* (2013.01)

(58) Field of Classification Search
  CPC ............... A61G 2210/70; A61F 7/0097; A61F 2007/0063; A61H 9/005; A61H 23/04; A61H 23/0245; A61H 23/006; A61H 9/0071; A61H 9/0078; A61H 2205/10; A61H 2201/10; A61H 2201/1654; A61H 2205/081; A61H 2203/0456; A61H 2201/5007; A61H 2201/1697; A61H 2033/0004; A61H 9/0021
  USPC .......................................................... 5/689
  See application file for complete search history.

(56) References Cited

U.S. PATENT DOCUMENTS

| | | | |
|---|---|---|---|
| 3,428,973 | A | 2/1969 | Hargest et al. |
| 3,492,988 | A | 2/1970 | Mare |
| 3,674,019 | A | 7/1972 | Grant |
| 3,866,606 | A | 2/1975 | Hargest et al. |
| 3,867,732 | A | 2/1975 | Morrell |
| 3,955,563 | A | 5/1976 | Maione et al. |
| 4,193,149 | A | 3/1980 | Welch |
| 4,224,706 | A | 9/1980 | Young et al. |
| 4,347,633 | A | 9/1982 | Gammons et al. |
| 4,371,997 | A | 2/1983 | Mattson |
| 4,394,784 | A | 7/1983 | Swenson et al. |
| 4,435,864 | A | 3/1984 | Callaway et al. |
| 4,481,686 | A | 11/1984 | Lacoste |
| 4,483,029 | A | 11/1984 | Paul |
| 4,508,107 | A | 4/1985 | Strom et al. |
| 4,517,693 | A | 5/1985 | Viesturs |
| 4,525,409 | A | 6/1985 | Elesh |
| 4,564,965 | A | 1/1986 | Goodwin |
| 4,599,755 | A | 7/1986 | Tominaga |
| 4,609,854 | A | 9/1986 | Yamamoto et al. |
| 4,628,557 | A | 12/1986 | Murphy |
| 4,637,083 | A | 1/1987 | Goodwin |
| 4,638,519 | A | 1/1987 | Hess |
| 4,684,486 | A | 8/1987 | Ricchio et al. |
| 4,686,722 | A | 8/1987 | Swart et al. |
| 4,689,844 | A | 9/1987 | Alivizatos |
| 4,694,520 | A | 9/1987 | Paul et al. |
| 4,694,521 | A | 9/1987 | Tominaga |
| 4,723,328 | A | 2/1988 | Kato et al. |
| 4,753,225 | A | 6/1988 | Vogel |
| 4,768,250 | A * | 9/1988 | Kato ................................ 5/689 |
| 4,794,659 | A | 1/1989 | Kurita et al. |
| 4,803,744 | A | 2/1989 | Peck et al. |
| 4,837,880 | A | 6/1989 | Coffman et al. |
| 4,879,777 | A | 11/1989 | Goodwin |
| 4,897,890 | A | 2/1990 | Walker et al. |
| 4,914,760 | A | 4/1990 | Hargest et al. |
| 4,942,635 | A | 7/1990 | Hargest et al. |
| 4,951,335 | A | 8/1990 | Eady |
| 4,967,431 | A | 11/1990 | Hargest et al. |
| 4,977,633 | A | 12/1990 | Chaffee |
| 4,982,466 | A | 1/1991 | Higgins et al. |
| 4,986,738 | A | 1/1991 | Kawasaki et al. |
| 4,991,244 | A | 2/1991 | Walker et al. |
| 4,993,920 | A | 2/1991 | Harkleroad et al. |
| 4,999,867 | A | 3/1991 | Toivio et al. |
| 5,007,123 | A | 4/1991 | Salyards |
| 5,008,965 | A | 4/1991 | Vrzalik |
| 5,018,786 | A | 5/1991 | Goldstein et al. |
| 5,029,352 | A | 7/1991 | Hargest et al. |
| 5,036,559 | A | 8/1991 | Hargest |
| 5,044,364 | A | 9/1991 | Crowther |
| 5,052,068 | A | 10/1991 | Graebe |
| 5,060,174 | A | 10/1991 | Gross |
| 5,062,169 | A | 11/1991 | Kennedy et al. |
| 5,068,933 | A | 12/1991 | Sexton et al. |
| 5,074,286 | A | 12/1991 | Gillaspie et al. |
| 5,083,335 | A | 1/1992 | Krouskop et al. |
| 5,095,568 | A | 3/1992 | Thomas et al. |
| 5,103,519 | A | 4/1992 | Hasty et al. |
| 5,109,560 | A | 5/1992 | Uetake |
| 5,109,561 | A | 5/1992 | Schild |
| 5,142,719 | A | 9/1992 | Vrzalik et al. |
| 5,152,021 | A | 10/1992 | Vrzalik et al. |
| 5,170,364 | A | 12/1992 | Gross et al. |
| 5,179,742 | A | 1/1993 | Oberle |
| 5,325,551 | A | 7/1994 | Tappel et al. |
| 5,331,698 | A | 7/1994 | Newkirk et al. |
| 5,335,384 | A | 8/1994 | Foster et al. |
| 5,367,728 | A | 11/1994 | Chang et al. |
| 5,375,273 | A | 12/1994 | Bodine et al. |
| 5,454,126 | A | 10/1995 | Foster et al. |
| 5,487,196 | A | 1/1996 | Wilkinson et al. |
| 5,539,943 | A | 7/1996 | Romano |
| 5,586,346 | A | 12/1996 | Stacy |
| 5,606,754 | A | 3/1997 | Hand et al. |
| 5,611,096 | A | 3/1997 | Bartlett et al. |
| 5,623,736 | A | 4/1997 | Soltani et al. |
| 5,666,681 | A | 9/1997 | Meyer et al. |
| 6,016,581 | A | 1/2000 | Miki |
| 6,073,289 | A | 6/2000 | Bolden et al. |
| 6,119,291 | A | 9/2000 | Osborne et al. |
| 6,158,070 | A * | 12/2000 | Bolden et al. ...................... 5/689 |
| 6,192,537 | B1 | 2/2001 | Miki |
| 6,202,672 | B1 * | 3/2001 | Ellis .................... A47C 27/082 137/223 |
| 6,302,145 | B1 | 10/2001 | Ellis et al. |
| 6,327,932 | B1 | 12/2001 | Onodera et al. |
| 6,351,862 | B1 | 3/2002 | Henley et al. |
| 6,353,948 | B1 | 3/2002 | Bolden et al. |
| 6,415,814 | B1 | 7/2002 | Hand et al. |
| 6,439,264 | B1 | 8/2002 | Ellis et al. |
| 6,564,412 | B2 | 5/2003 | Henley et al. |
| 6,574,813 | B2 | 6/2003 | Bolden et al. |
| 6,694,555 | B2 | 2/2004 | Soltani et al. |
| 6,721,979 | B1 | 4/2004 | Vrzalik et al. |
| 6,735,801 | B2 | 5/2004 | Henley et al. |
| 6,820,640 | B2 | 11/2004 | Hand et al. |
| 6,953,439 | B1 | 10/2005 | Kabemba |
| 7,107,642 | B2 | 9/2006 | Wong et al. |
| 7,219,380 | B2 | 5/2007 | Beck et al. |
| 7,451,506 | B2 | 11/2008 | Kummer et al. |
| 7,458,119 | B2 | 12/2008 | Hornbach et al. |
| 7,509,698 | B2 | 3/2009 | Poulos |

(56) References Cited

U.S. PATENT DOCUMENTS

| | | | |
|---|---|---|---|
| 7,536,739 B2 | 5/2009 | Poulos | |
| 7,587,776 B2 | 9/2009 | Poulos | |
| 7,641,623 B2 | 1/2010 | Biondo et al. | |
| 7,657,956 B2* | 2/2010 | Stacy et al. | 5/713 |
| 7,698,765 B2 | 4/2010 | Bobey et al. | |
| 7,716,766 B2 | 5/2010 | Poulos | |
| 7,802,332 B2 | 9/2010 | Kummer et al. | |
| 7,975,335 B2 | 7/2011 | O'Keefe et al. | |
| 8,038,632 B2 | 10/2011 | Flick et al. | |
| 8,056,165 B2 | 11/2011 | Kummer et al. | |
| 8,108,957 B2 | 2/2012 | Richards et al. | |
| 8,146,191 B2 | 4/2012 | Bobey et al. | |
| 8,151,391 B2 | 4/2012 | Frias | |
| 8,196,240 B2 | 6/2012 | Meyer et al. | |
| 8,286,282 B2 | 10/2012 | Kummer et al. | |
| 8,397,326 B2 | 3/2013 | Lafleche et al. | |
| 8,397,327 B2 | 3/2013 | O'Reagan | |
| 8,413,271 B2 | 4/2013 | Blanchard et al. | |
| 8,474,074 B2 | 7/2013 | O'Keefe et al. | |
| 8,572,778 B2 | 11/2013 | Newkirk et al. | |
| 8,584,279 B2 | 11/2013 | Richards et al. | |
| 8,590,731 B2 | 11/2013 | Pinelli | |
| 8,603,017 B2 | 12/2013 | Trandafir et al. | |
| 8,707,483 B2 | 4/2014 | Richards et al. | |
| 8,727,176 B2 | 5/2014 | Ei-Saden et al. | |
| 8,734,370 B1 | 5/2014 | Ignagni | |
| 8,789,222 B2 | 7/2014 | Blanchard et al. | |
| 8,795,210 B2 | 8/2014 | Talish et al. | |
| 8,803,682 B2 | 8/2014 | Wong et al. | |
| 8,832,885 B2 | 9/2014 | Lafleche et al. | |
| 2001/0052152 A1 | 12/2001 | Soltani | |
| 2006/0053558 A1* | 3/2006 | Ye | 5/689 |
| 2006/0168736 A1* | 8/2006 | Meyer et al. | 5/727 |
| 2008/0235872 A1 | 10/2008 | Newkirk et al. | |
| 2008/0263776 A1* | 10/2008 | O'Reagan et al. | 5/714 |
| 2011/0138538 A1* | 6/2011 | Howell | 5/689 |
| 2011/0296623 A1 | 12/2011 | Lafleche et al. | |
| 2011/0296624 A1 | 12/2011 | Lafleche et al. | |
| 2012/0096644 A1 | 4/2012 | Heimbrock | |
| 2012/0172959 A1 | 7/2012 | Lachenbruch et al. | |
| 2013/0074271 A1 | 3/2013 | Klink et al. | |

FOREIGN PATENT DOCUMENTS

| | | |
|---|---|---|
| EP | 317009 A1 | 1/1992 |
| EP | 332242 A2 | 8/1992 |
| EP | 1723877 A1 | 11/2006 |
| EP | 1139966 B1 | 5/2008 |
| EP | 2233118 A2 | 9/2010 |
| EP | 1901635 B1 | 5/2013 |
| EP | 2586413 A2 | 5/2013 |
| EP | 2682085 A1 | 1/2014 |
| FR | 2546403 A1 | 11/1984 |
| FR | 2897774 A1 | 8/2007 |
| GB | 2457702 A | 8/2009 |
| JP | S6122860 A | 1/1986 |
| WO | 9841180 A1 | 9/1998 |
| WO | 2007008723 A2 | 1/2007 |
| WO | 2007047379 A2 | 4/2007 |
| WO | 2011097569 A2 | 8/2011 |

OTHER PUBLICATIONS

Search report for related European Application No. 15158895.1-1658, dated Jul. 20, 2015, 6 pages.
Extended Search report for related European Application No. 15158895.1-1658, dated Nov. 5, 2015, 6 pages.
European Office Action for EP Application No. 16172750.8, dated Jun. 22, 2018, 6 pages.

\* cited by examiner

FIG. 12

AIR FLUIDIZED THERAPY BED HAVING PULMONARY THERAPY

CROSS-REFERENCE TO RELATED U.S. APPLICATION

This present application claims priority under 35 U.S.C. § 119(e) to U.S. Provisional Patent Application Ser. No. 61/778,789, entitled "AIR FLUIDIZED THERAPY BED HAVING PULMONARY THERAPY," which was filed on Mar. 13, 2013, the entirety of which is hereby incorporated by reference.

BACKGROUND

The present disclosure is related to patient support apparatuses that provide air fluidized therapy. More specifically, the present disclosure is related to patient support apparatuses that provide air fluidized therapy and additional therapies utilizing the functionality of the air fluidized therapy system of the patient support apparatus.

Patient support apparatuses that provide air fluidized therapy are well known in the art and are considered to be a specialized use device that supports at least a portion of the patient on the air fluidized section when the patient has highly compromised skin. For example burn patients, severe diabetics, or compromised elderly patients may be supported on the air fluidized therapy which has been shown to help reduce further injury and promote healing of the compromised skin. In general, patient support apparatuses that provide air fluidized therapy do not provide other therapies may be found in beds or mattresses that do not provide air fluidized therapy.

SUMMARY

The present application discloses one or more of the features recited in the appended claims and/or the following features which, alone or in any combination, may comprise patentable subject matter:

According to a first aspect of the present disclosure, a patient support apparatus comprises an air supply, an air fluidization therapy bed, and a pulsator coupled to the air fluidization therapy bed. The air fluidization therapy bed includes a fluidization space and a fluidizable medium positioned in the fluidization space. The air fluidization therapy bed receives a flow of pressurized air from the air supply. The flow of pressurized air is operable to fluidize the fluidizable medium. The pulsator is positioned to transmit air pulses through the fluidized fluidizable medium to impart a percussive force to a body supported on air fluidization therapy bed.

In some embodiments, the pulsator is in fluid communication with the air supply and operable to form air pulses from at least a portion of the flow from the air supply.

In some embodiments, the frequency and magnitude of the air pulses are variable.

In some embodiments, the patient support apparatus further comprises a percussion/vibration controller operable to control the operation of the pulsator.

In some embodiments, the patient support apparatus further comprises a controller and a user interface, the user interface isoperable to receive inputs from a user indicative of at least one desired operating parameter of the percussion/vibration controller, the controller operable to modify the operation of the percussion/vibration controller to achieve the desired operating parameter.

In some embodiments, the patient support apparatus comprises a first conduit, a tap coupled to the first conduit, a second conduit coupled to the tap and the pulsator, a third conduit coupled to the tap and the air fluidization therapy bed, the third conduit smaller than the first conduit and the second conduit.

In some embodiments, the pulsator comprises a valve that is openable to allow air to flow through the second conduit and the valve of the pulsator. In some embodiments, the valve of the pulsator is in communication with the space of the air fluidization therapy bed such that when the valve opens, air flows through the valve into the space. In some embodiments, the valve opens and closes to create air pulses in the space of the air fluidization therapy bed.

In some embodiments, the air supply has a variable output, the output being modified to compensate for the flow of air used to provide the percussive forces.

According to another aspect of the present disclosure, a patient support apparatus comprises an air supply, a first patient support zone comprising an air fluidization therapy bed, a second patient support zone comprising a plurality of inflatable support bladders, and a sonic emitter. The first patient support zone includes a fluidization space and a fluidizable medium positioned in the fluidization space. The air fluidization therapy bed receives a flow of pressurized air from the air supply. The flow of pressurized air is operable to fluidize the fluidizable medium. The sonic emitter is coupled to the second portion and positioned to transmit sonic waves through the bladders to impart a percussive force to a body supported on the second portion.

In some embodiments, the sonic emitter has a variable frequency and amplitude.

In some embodiments, the patient support apparatus further comprises a sonic controller operable to control the frequency and amplitude of the sonic emitter.

In some embodiments, the patient support apparatus further includes a controller operable to control the fluid supply and the sonic controller.

In some embodiments, the patient support apparatus further includes a user interface, the user interface operable to accept a user input indicative of a desired operating parameter of the sonic emitter.

In some embodiments, the controller modifies operation of the sonic controller to achieve the desired operating parameter of the sonic emitter.

In some embodiments, the second patient support zone is movable relative to the first patient support zone.

In some embodiments, the sonic emitter is coupled to the second patient support zone to move therewith.

According to yet another aspect of the present disclosure, a patient support apparatus comprises an air supply, a first patient support zone comprising an air fluidization therapy bed, a second patient support zone comprising a plurality of inflatable support bladders, and a percussion assembly. The first patient support zone comprises a fluidization space and a fluidizable medium positioned in the fluidization space. The air fluidization therapy bed receives a flow of pressurized air from the air supply. The flow of pressurized air is operable to fluidize the fluidizable medium. The percussion assembly is coupled to the second portion. The percussion assembly includes a plurality of chambers. Each chamber includes a vent and is positioned to impart a percussive force to a body supported on the second portion when the chamber is inflated.

In some embodiments, the patient support apparatus further comprises a plurality of conduits, each conduit coupled to a respective chamber. In some embodiments, the patient support apparatus comprises a plurality of valves, each valve associated with one of the conduits coupled to a respective chamber. In some embodiments, the patient support apparatus includes a percussion/vibration controller that is operable to control the operation of the valves to selectively inflate the chambers. In some embodiments, the valves are coupled to the air supply such that opening of one of the plurality of valves permits a flow of air from the air supply to a respective chamber. In some embodiments, the vents of the chambers are sized such that they constrict flow out of each chamber, and wherein the flow of the air from the air supply is sufficient to rapidly expand the chamber when a valve is opened, the vent allowing the expanded chamber to contract when the valve is closed.

In some embodiments, the patient support apparatus further comprises a percussion/vibration controller operable to control the frequency and amplitude of the inflations of the chambers.

In some embodiments, the patient support apparatus further includes a controller operable to control the fluid supply and the percussion/vibration controller.

In some embodiments, the patient support apparatus further includes a user interface, the user interface operable to accept a user input indicative of a desired operating parameter of the percussion/vibration controller.

In some embodiments, the controller modifies operation of the percussion/vibration controller to achieve the desired operating parameter of the percussion/vibration controller.

In some embodiments, the second patient support zone is movable relative to the first patient support zone.

In some embodiments, the percussion assembly is coupled to the second patient support zone to move therewith.

According to still another aspect of the present disclosure, a patient support apparatus comprises an air supply, a first patient support zone comprising an air fluidization therapy bed, and a garment coupled to the air supply. The air fluidization therapy bed includes a fluidization space and a fluidizable medium positioned in the fluidization space. The air fluidization therapy bed receives a flow of pressurized air from the air supply. The flow of pressurized air is operable to fluidize the fluidizable medium. The garment includes a plurality of chambers. Each chamber includes a vent. Each chamber is positioned to impart a percussive force to a the body of a patient wearing the garment when a chamber is inflated.

In some embodiments, the patient support apparatus further comprises a plurality of conduits, each conduit coupled to a respective chamber.

In some embodiments, the patient support apparatus comprises a plurality of valves, each valve associated with one of the conduits coupled to a respective chamber.

In some embodiments, the patient support apparatus includes a percussion/vibration controller that is operable to control the operation of the valves to selectively inflate the chambers.

In some embodiments, the valves are coupled to the air supply such that opening of one of the plurality of valves permits a flow of air from the air supply to a respective chamber.

In some embodiments, the vents of the chambers are sized such that they constrict flow out of each chamber, and wherein the flow of the air from the air supply is sufficient to rapidly expand the chamber when a valve is opened, the vent allowing the expanded chamber to contract when the valve is closed.

In some embodiments, the patient support apparatus further comprises a percussion/vibration controller operable to control the frequency and amplitude of the inflations of the chambers.

In some embodiments, the patient support apparatus further includes a controller operable to control the fluid supply and the percussion/vibration controller.

In some embodiments, the patient support apparatus further includes a user interface, the user interface operable to accept a user input indicative of a desired operating parameter of the percussion/vibration controller.

In some embodiments, the controller modifies operation of the percussion/vibration controller to achieve the desired operating parameter of the percussion/vibration controller.

In some embodiments, the patient support apparatus further comprises a second patient support zone comprising a plurality of inflatable support bladders.

In some embodiments, the second patient support zone is movable relative to the first patient support zone.

According to still another aspect of the present disclosure, a patient support apparatus comprises an air supply, a first patient support zone comprising an air fluidization therapy bed, a second patient support zone comprising a plurality of inflatable support bladders, and a micro-climate assembly coupled to the second portion. The air fluidization therapy bed includes a fluidization space and a fluidizable medium positioned in the fluidization space. The air fluidization therapy bed receives a flow of pressurized air from the air supply. The flow of pressurized air is operable to fluidize the fluidizable medium. The micro-climate assembly includes an upper layer of vapor permeable material and a lower layer coupled to the upper layer to define a chamber having an inlet and an outlet. The chamber defines an interior space. A three dimensional material is positioned in the interior space. The micro-climate assembly is coupled to the air supply to selectively receive a flow of pressurized air from the air supply. The flow of air enters the chamber through the inlet and exiting the chamber through the outlet.

In some embodiments, the patient support apparatus includes a first conduit from the air supply to the air fluidization therapy bed.

In some embodiments, the patient support apparatus further comprises a valve coupled to the first conduit and a second conduit coupled to the valve, the second conduit coupled to the micro-climate assembly.

In some embodiments, the patient support apparatus further comprises a controller operable to control the valve to selectively direct a flow of air from the air supply to the micro-climate assembly.

In some embodiments, the patient support apparatus further includes a sonic emitter operable to impart a percussive force to a patient supported on the patient support apparatus.

In some embodiments, the patient support apparatus further includes a garment coupled to the air supply, the garment including a plurality of chambers, each chamber including a vent and positioned to impart a percussive force to a the body of a patient wearing the garment when the chamber is inflated.

In some embodiments, the patient support apparatus further includes a percussion assembly coupled to the second portion, the percussion assembly including a plurality of chambers, each chamber including a vent and positioned to impart a percussive force to a body supported on the second portion when the chamber is inflated.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
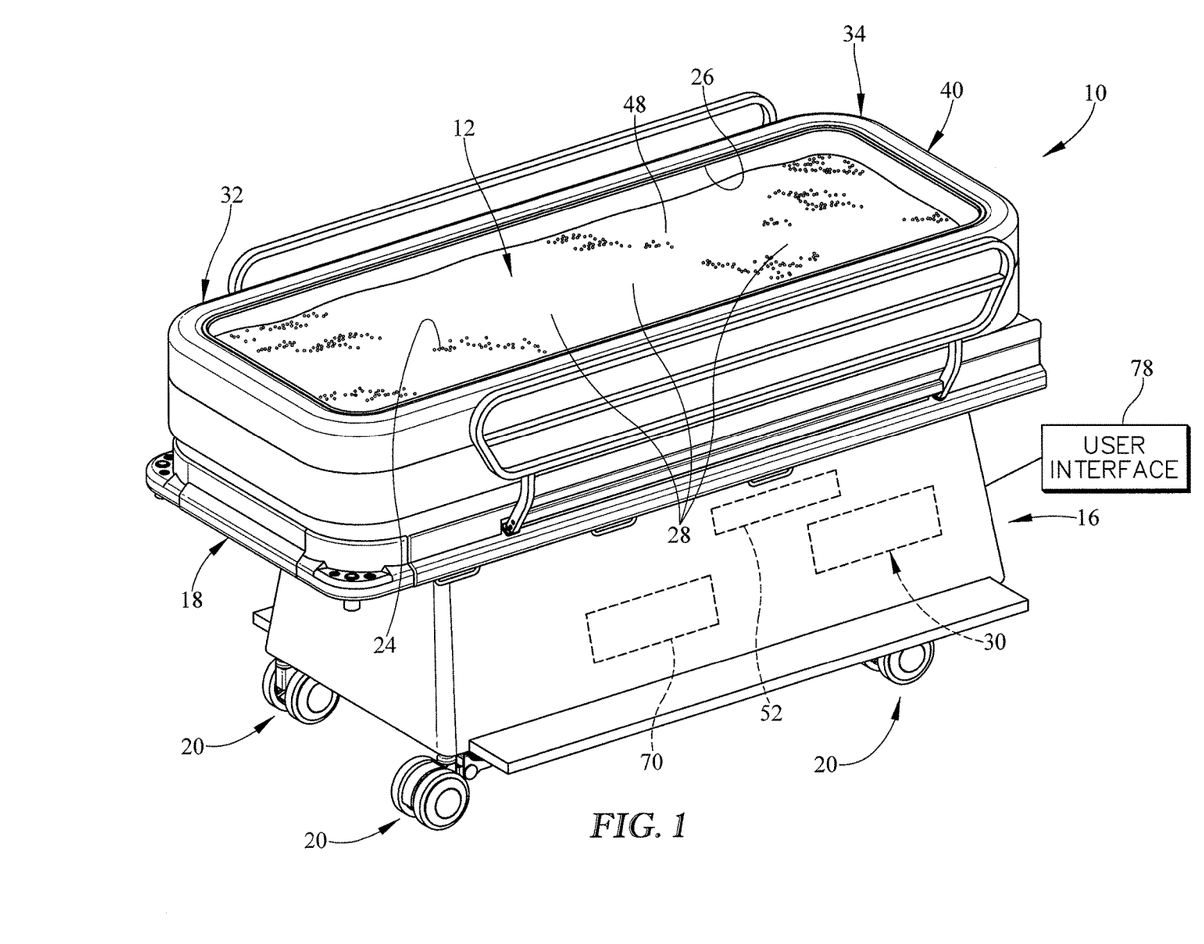
FIG. 1 is a perspective view of a patient support apparatus that includes an air fluidized therapy bed and a pulsator for delivery a percussive force to the body of a patient supported on a surface of the patient support apparatus.

A patient support apparatus 10, illustratively embodied as an air fluidized therapy bed, includes a surface 12 on which a patient who has highly compromised skin may be positioned to receive therapy is shown in FIG. 1. The patient support apparatus 10 includes a lower frame 16 that supports a tank 14, the tank 14 supports a fluidized air bed covered by a filter sheet 24. The filter sheet 24 is configured to allow air to pass through the filter sheet 24 while containing fluidizable medium 28, embodied as silica beads, within the tank 14.

The patient support apparatus 10 includes a head end 34 and a foot end 32. The lower frame 16 is supported on a plurality of casters 20 which facilitate movement of the patient support apparatus 10 over a floor. The lower frame 16 supports an upper frame 18 upon which the tank 14 is mounted. In other embodiments, the perimeter structure may be an inflatable bladder. An air supply 30 is supported on the lower frame 16 and provides a high volume of pressurized air to the tank 14 to fluidize the fluidizable medium 28 as will be discussed in further detail below.

Figure 2:
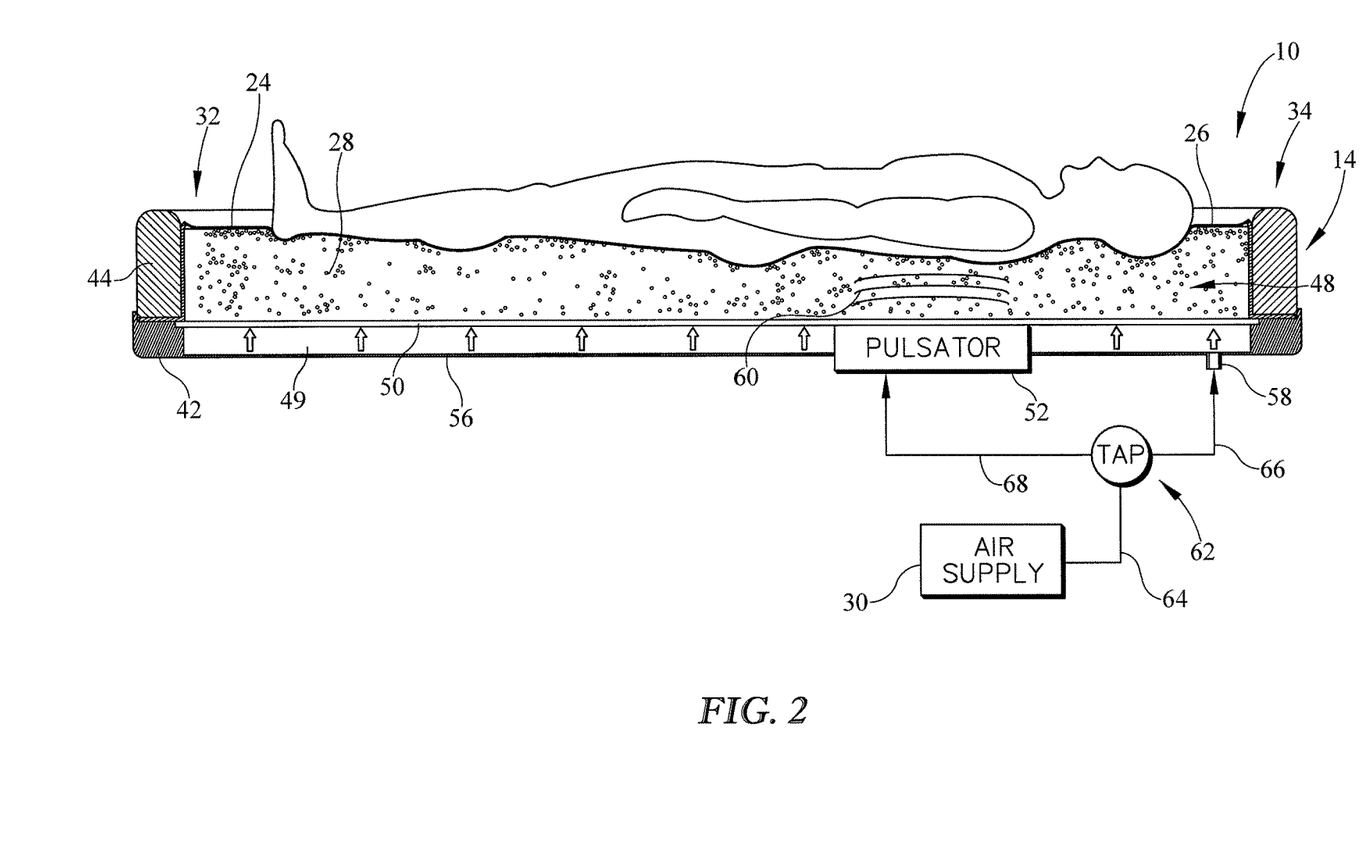
FIG. 2 is a cross-sectional view of a portion of the patient support apparatus of FIG. 1 with a patient supported on a surface of the air fluidized therapy bed.

Referring now to FIG. 2, the air supply 30 is pneumatically coupled to an inlet 58 which conveys the air from the air supply 30 into a space 48 formed between a tub bottom 56 and a diffuser 50. The space 49 acts as a manifold so that air transferred into the space 48 is evenly distributed throughout the space 48 and urged through the diffuser 50. When the pressure in the space 49 becomes excessive, air flows through the diffuser 50 into the fluidizable medium 28 and creates an air fluidized bed for supporting a patient 36. The filter sheet 24 further limits the flow of air so that the patient 36 "floats" on the air fluidized therapy bed 10. Air fluidization therapy (AFT) spreads the weight of the patient 36 over the surface 12 and reduces the interface pressure experienced by the patient's skin on the AFT bed 10.

Because patients who require AFT tend to be quite ill and in a highly compromised state, they often require other therapeutic treatments beyond the AFT available on the AFT bed 10. In the illustrative embodiment of FIG. 2, the AFT bed 10 further includes a pulsator 52 which is operable to generate independent pulse waves 60 through the fluidized bed to deliver percussion and/or vibration therapy to a patient supported on the AFT bed 10.

The tank 14 includes a tank base 42, a tank liner 40, a tank bladder 44, and the filter sheet 24 as shown in FIG. 2. In one illustrative embodiment, the tank base 42 and the tank liner 40 are made of a low or substantially no air-loss material, such as, for example, a polyurethane-backed nylon fabric material, and the tank bladder 44 is composed of a substantially no air loss polymeric material and filled with a fluid, such as, air. The tank base 42 is coupled to the upper frame 18 by tank fasteners (not shown) and includes the inlet 58 that couples to the air supply 30. The tank liner 40 and the tank bladder 44 are coupled together to form the sides of the tank 14. The tank base 42 is coupled with the tank liner 40 and the tank bladder 44 to define an opening 26 arranged to open into the tank 14 as shown in FIG. 2.

The filter sheet 24 is positioned over the opening 26 and is coupled to the tank liner 40 as shown in FIG. 2. The filter sheet 24 is coupled to the tank liner 40 by fasteners which may be zippers, buttons, snaps, turn-buttons, hook and loop fasteners, or any other suitable alternative. The tank base 42, the tank liner 40, the tank bladder 44, and the filter sheet 24 cooperate to define the space 48 therebetween that contains the fluidizable medium 28. The filter sheet 24 is configured to allow fluid, such as, bodily fluids and air, to pass therethrough while preventing the fluidizable medium 28 from passing through. The filter sheet 24 is also configured to provide sufficient support to minimize or eliminating hammocking from occurring when a patient 36 is supported by the fluidized fluidizable medium 28 so that the patient 36 is properly supported.

The diffuser 50 is configured to support the fluidizable medium 28 thereon and provide substantially uniform fluid flow to the fluidizable medium 28 from the air supply 30 as suggested, for example, in FIG. 2. Air supplied by the air supply 30 passes through the diffuser 50 and into the fluidizable medium 28 to cause the fluidizable medium 28 to become fluidized. Further disclosure of an air fluidization therapy bed may be found in U.S. application Ser. No. 13/246,886, filed Sep. 28, 2011 and entitled SYSTEMS, METHODS, AND DEVICES FOR FLUIDIZING A FLUIDIZABLE MEDIUM, which is incorporated in its entirety by reference herein.

Figure 3:
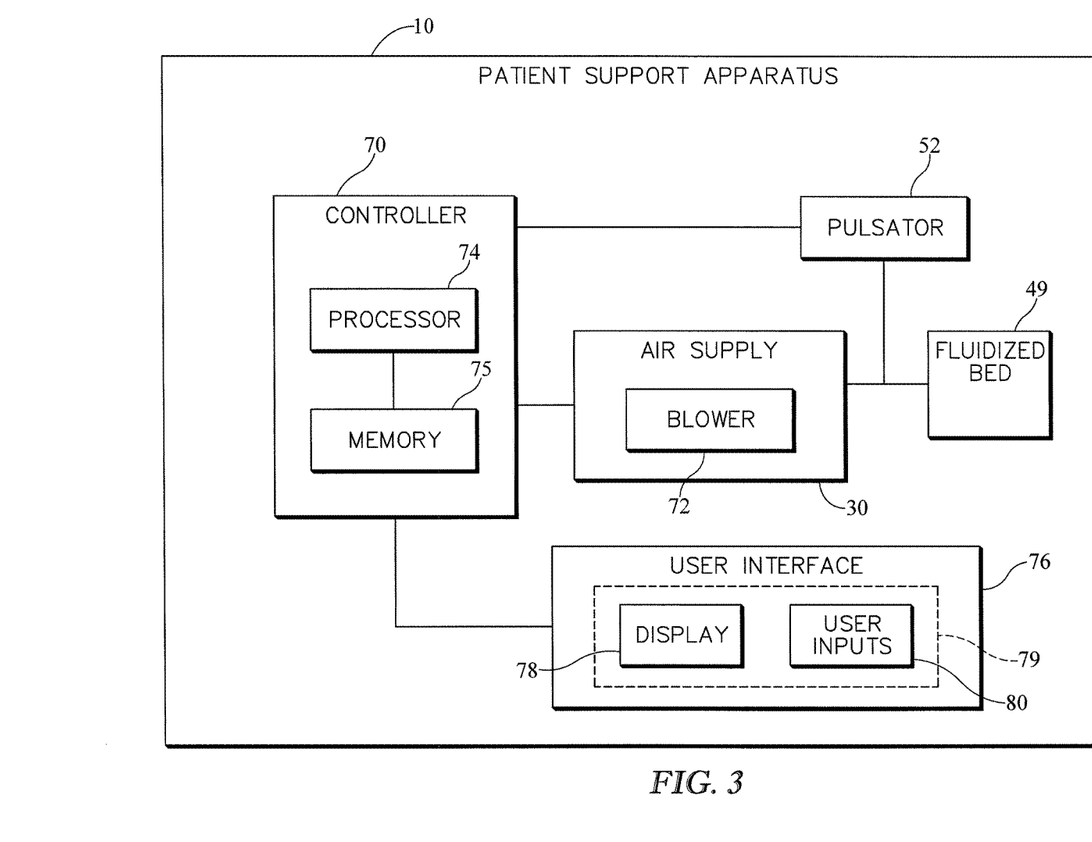
FIG. 3 is a block diagram of the control system of the patient support apparatus of FIG. 1.

The pulsator 52 receives air from the air supply 30 through a tap 62 from a conduit 64 between the air supply 30 and the inlet 58. The pulsator 52 includes a quick acting valve that opens and closes very quickly. The flow path through a conduit 66 from the tap 62 to the inlet 49 has a first diameter that tends to limit flow from the air supply 30 into the space 48. A conduit 68 from the tap 62 to the pulsator 52 allows for a higher flow of air to pass therethrough and to the pulsator 52. The pulsator 52, under the control of a controller 70 as shown in the block diagram in FIG. 3, is operated to allow bursts of air to flow into the tank 14, the bursts of air traveling through the tank 14 to impinge upon the upper body of the patient 36. By controlling the duration of time that the valve of the pulsator 52 is open, the magnitude of the air bursts can be varied. In addition, modification of the time between valve openings controls the frequency of the bursts or pulses. Percussion therapy may be achieved by providing large bursts at a lower frequency, while vibration is imparted with small bursts at a high frequency. Generally, the range of frequencies may be varied from 1 to 20 Hz.

The AFT bed 10 includes the controller 70 that operates both the pulsator 52 and the air supply 30. The air supply 30 includes a variable speed blower 72 that is operable to vary the volume of air flowing through the conduit 64, under the control of a processor 74 which is in communication with a memory device 75, the memory device 75 including instructions that, when executed by the processor 74 causes the processor 74 to control operation of the patient support apparatus 10. In addition, the AFT bed 10 includes a user interface 76 that includes a display 78 and a plurality of user inputs 80 that are operable to change the operation of the AFT bed 10. For example, a user may choose to activate the pulsator 52 and may choose a frequency, magnitude, and duration of the percussion/vibration therapy. In addition, a user may vary the speed of the blower 72 to adjust the fluidization of the fluidizable medium 28. In the illustrative embodiment, the user interface 76 includes a touchscreen 79 that also includes the user inputs 80 on the display. In other embodiments, the display 78 may be a simple multi-segment LED display and the user inputs 80 may be discrete buttons or switches.

Figure 4:
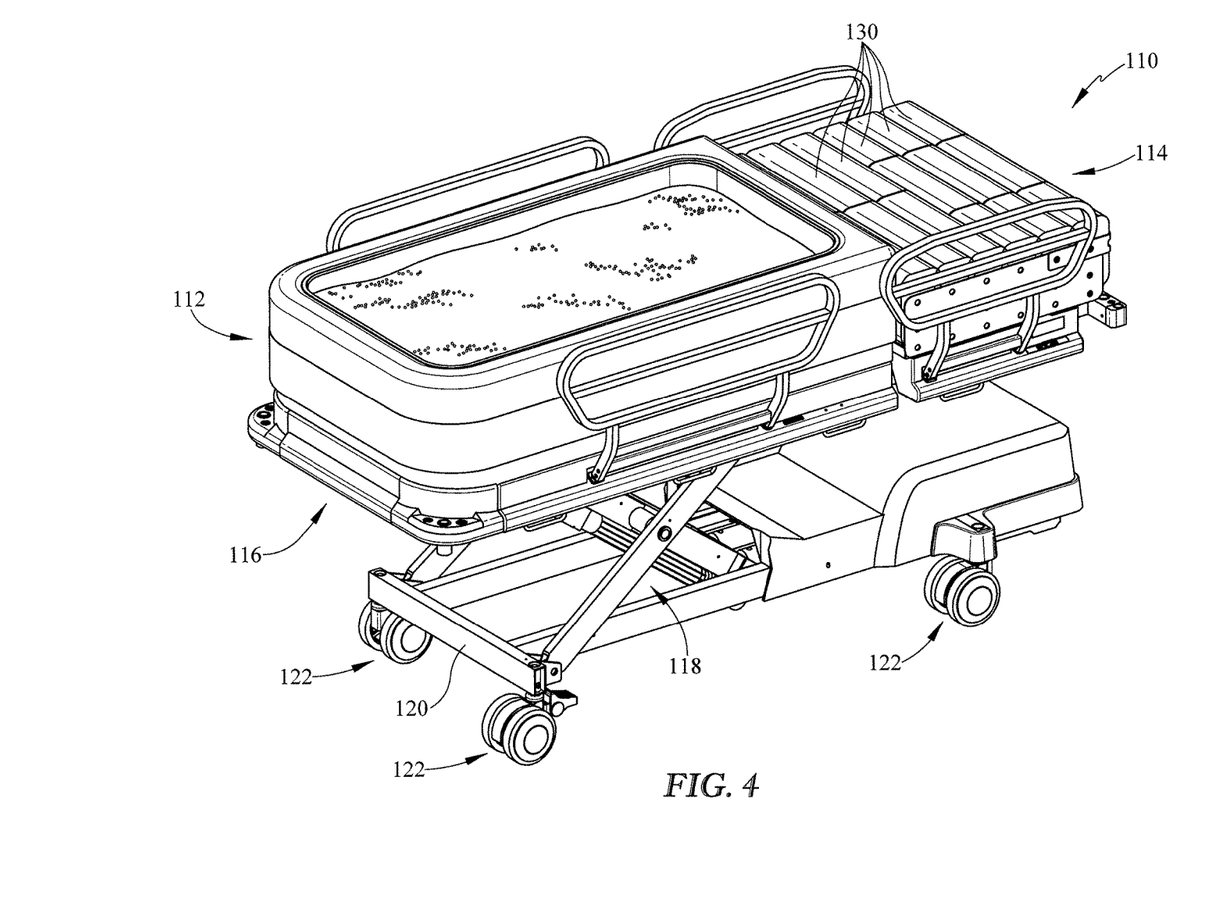
FIG. 4 is a perspective view of another embodiment of a patient support apparatus that includes a first section that includes an air fluidized therapy bed similar to the embodiment of FIG. 1 and a second portion that includes a plurality of bladders for supporting a portion of a patient.

In another embodiment shown in FIG. 4, a patient support apparatus 110 is illustratively embodied as a therapeutic bed that includes a first portion 112 that provides AFT to the lower body of a patient supported on the patient support apparatus 110. The first portion 112 is constructed similarly to the embodiment of FIGS. 1-3, with the first portion 112 being sized to support the lower body of a patient. A second portion 114 is configured to support the upper body of the patient supported on the patient support apparatus 110. The second portion 114 includes a plurality of bladders 130 that are inflated to a pressure which is optimized to reduce the incidence of the development of decubitus ulcers, also known as bedsores. The patient support apparatus 110 of the present disclosure includes a lower frame 120 supported on a plurality of casters 122. A lift system 118 is coupled to the lower frame 120 and supports an upper frame 116. The first portion 112 is fixed and maintained in a horizontal position by the upper frame 116. The second portion 114 is supported on the upper frame 116 and is pivotable relative to the upper frame 116 and the first portion 112 to increase the elevation of the head and upper body of a patient supported on the patient support apparatus 110.

The present disclosure includes embodiments that deliver additional therapies, generally pulmonary therapies, to patients who are candidates for air fluidized therapy. In the embodiment shown in FIGS. 4-7, the second portion 114 includes a sonic emitter 134 which is positioned below the bladders 130 and operable to generate sonic pulses that travel through the bladders 130 and impart a percussive or vibrational force to the upper body of a patient 36 supported on the second portion 114 of patient support apparatus 110.

Figure 5:
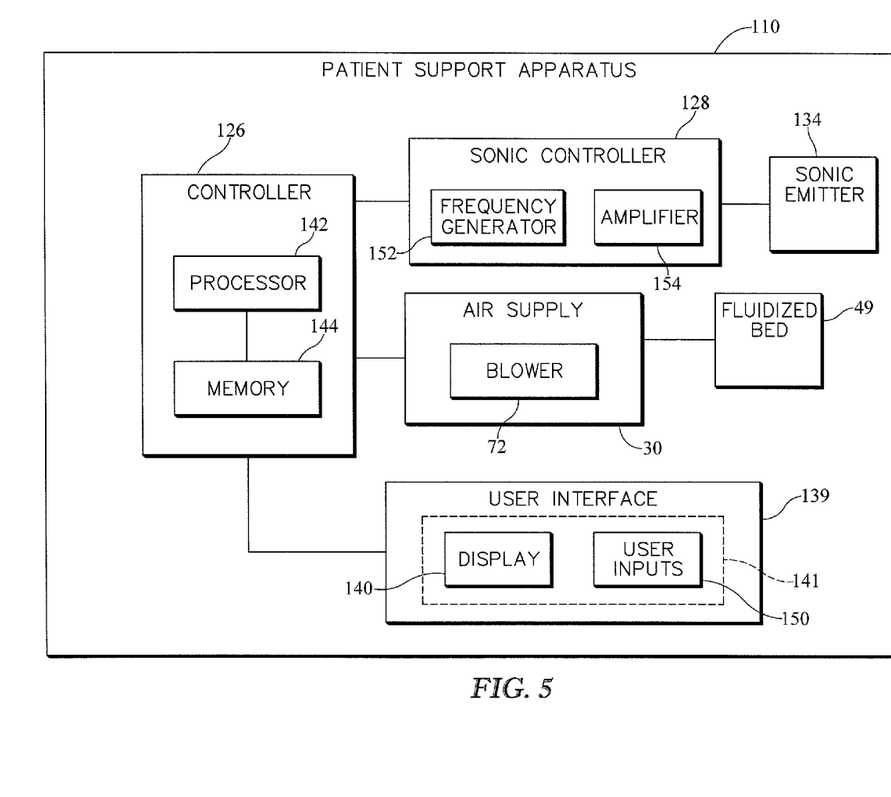
FIG. 5 is a block diagram of the control system of the patient support apparatus of FIG. 4.

Referring to FIG. 5, the patient support apparatus 110 includes a controller 126 that has processor 142 in communication with a memory device 144, the controller 126 is operable to control all of the operations of the patient support apparatus 110. Patient support apparatus 110 also includes a user interface 139 that has a graphical display screen 140 and a number of user inputs 150 as will be described in further detail below. The user interface 139 may optionally include a touchscreen 141 that acts as both the graphical display screen 140 and user inputs 150. The controller 126 is operable to control a fluid supply 124 that generates a flow of air similar to the manner described above with reference to the patient support apparatus 10.

The controller 126 also controls a sonic controller 128 which is operable to drive the sonic emitter 134 to generate sonic waves through the bladders 130 which then impinge upon the upper body of a patient supported on the second portion 114. The sonic controller 128 includes a frequency generator 152 and an amplifier 154. A user is able to select a particular percussive or vibration therapy from the user interface 139 which controls the magnitude and frequency of the sonic pulses from the sonic emitter 134.

Figure 6:
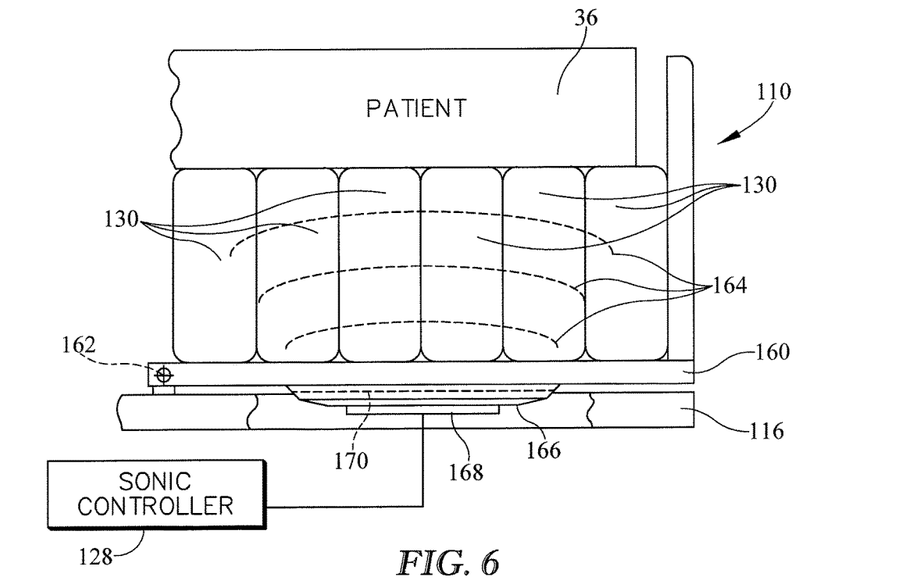
FIG. 6 is a side view of the second portion of the patient support apparatus of FIG. 4, the second portion in a first orientation.
Figure 7:
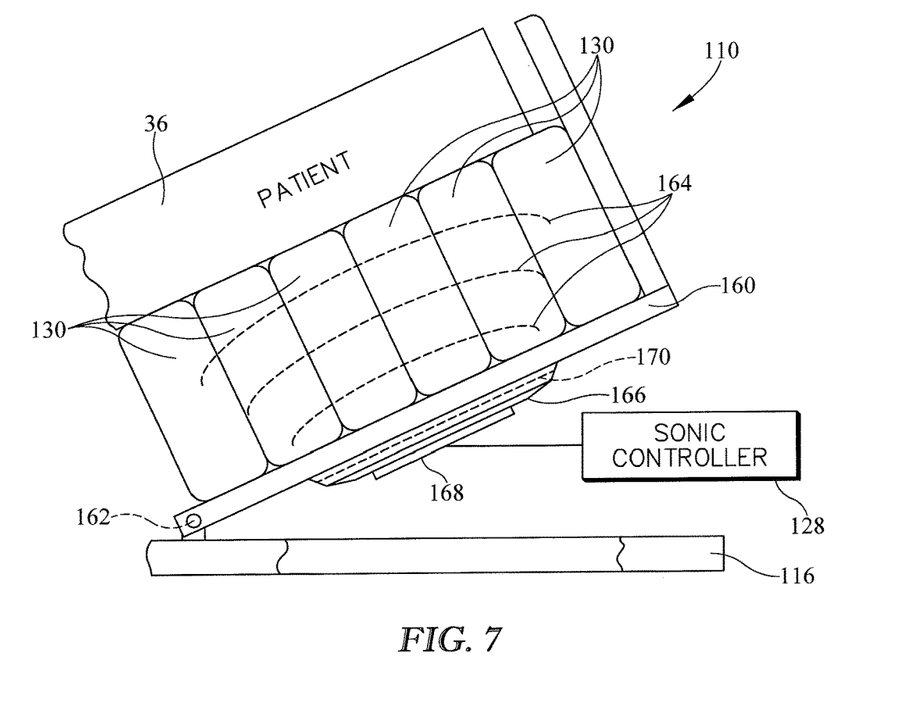
FIG. 7 is a side view similar to FIG. 6, the second portion in a second orientation.

Referring now to FIGS. 6 and 7, the patient support apparatus 110 includes a head deck section 160 that is pivotably coupled to the upper frame 116 of the patient support apparatus 110 and pivotable about an axis 162. The sonic emitter 134 is fixed to the head deck section 160 such that sonic energy is transferred through the head deck section 160 into the bladders 130. The sonic energy, in the form of sonic waves 164 travel through the bladders 130 to impact the patient 36. As depicted in FIG. 7, the sonic emitter 134 is embodied as a traditional speaker including a body 166, a driver 168 that includes a coil and permanent magnet, the coil is coupled to a diaphragm 170 that moves relative to the body 166 to create the waves 164.

Being coupled to the head deck section 160, the sonic emitter 134 moves with the head deck section 160 as it pivots about the axis 162. Thus, percussion and/or vibration therapy may be delivered to the patient 36 as the head deck section 160 moves between a lowered position as shown in FIG. 6 and a raised position as shown in FIG. 7.

Figure 8:
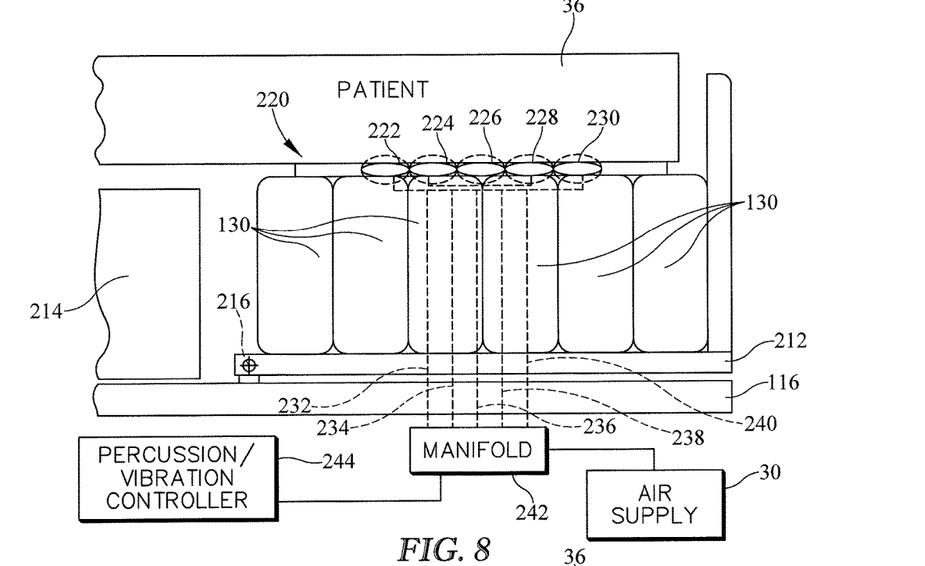
FIG. 8 is a side view of another embodiment of a second portion of a patient support apparatus similar to the embodiment of FIG. 4, the second portion including a percussion assembly in a first orientation.
Figure 9:
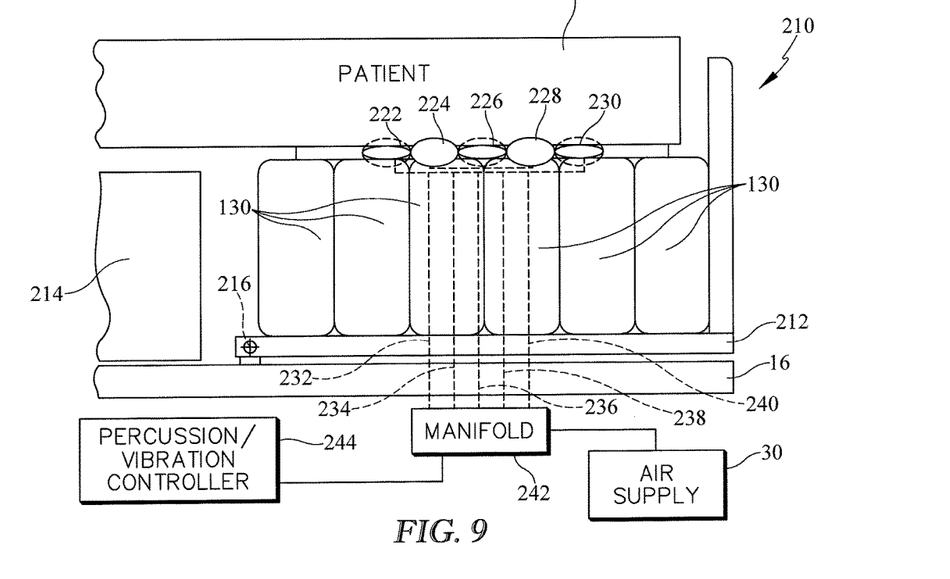
FIG. 9 is a side view of similar to FIG. 8, the second portion including a percussion assembly in a second orientation.
Figure 10:
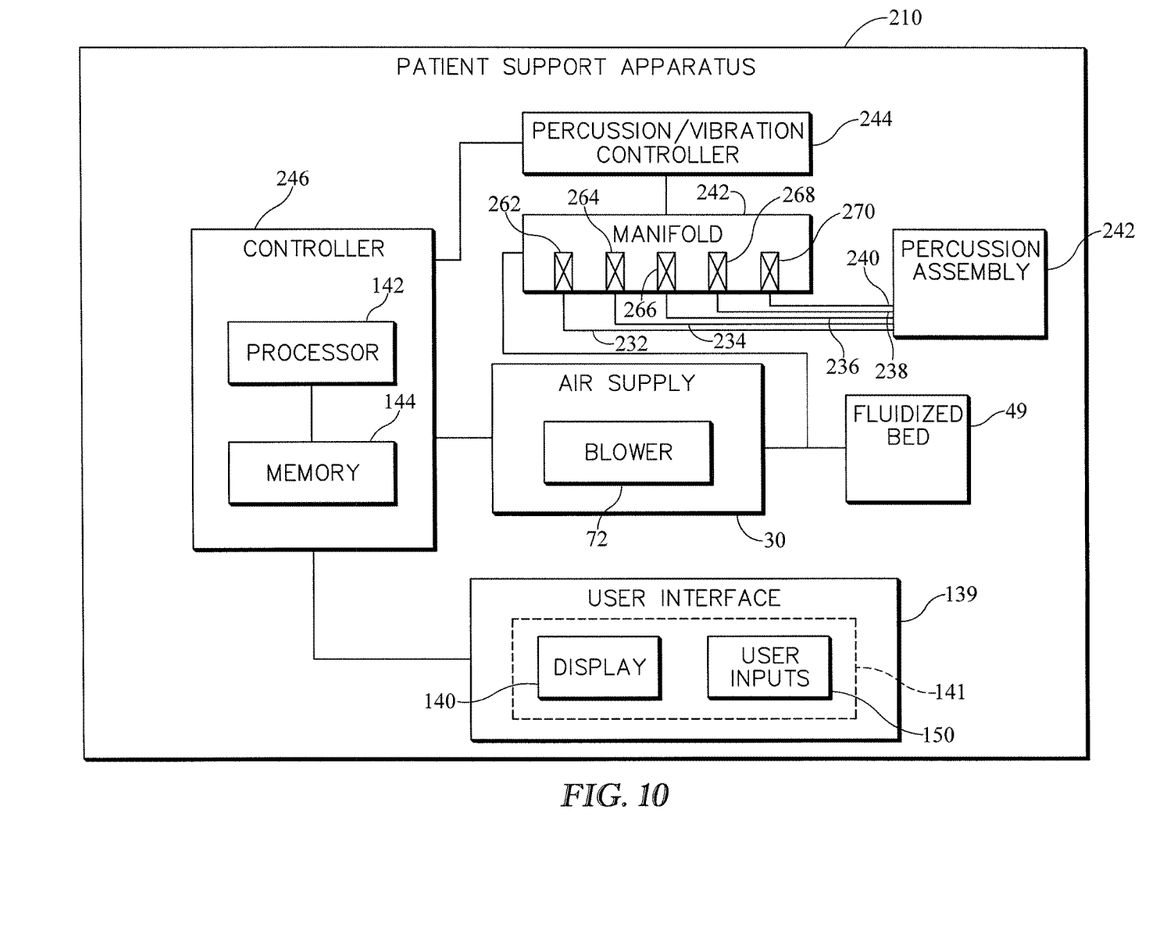
FIG. 10 is a block diagram of the control system of the embodiment of patient support apparatus of FIGS. 8 and 9.

In yet another embodiment, shown in FIGS. 8-10, a patient support apparatus 210 is similar to the patient support apparatus 110, but the sonic controller and sonic emitter are omitted. The patient support apparatus 210 includes a head deck section 212 which is pivotably coupled to an upper frame 116 and pivotable about an axis 216. The patient support apparatus 210 has a different second portion 214 from second portion 114 of patient support apparatus 110 in that patient support apparatus 210 includes a percussion and vibration bladder assembly 220 that is supported on the top of the bladders 130. The percussion and vibration bladder assembly 220 includes five chambers 222, 224, 226, 228, and 230, each of which is coupled to a respective conduit 232, 234, 236, 238, 240 which are fed from a manifold 242. The manifold 242 is in communication with the air supply 30 of the patient support apparatus 210. The air supply 30 provides a flow of air to the first portion 112 of the patient support apparatus 210. The manifold 242 includes a number of valves 262, 264, 266, 268, 270 (shown in FIG. 10) which operate similarly to the pulsator 52.

Referring to the block diagram of FIG. 10, the respective valves 262, 264, 266, 268, 270 of the manifold 242 are under the control of a percussion/vibration controller 244. The patient support apparatus 210 includes a controller 246 similar to the controller 126 and configured to control the patient support apparatus 210, but the sonic controller 128 is omitted and replaced with the percussion/vibration controller 244. The percussion/vibration controller 244 is operable to control the operation of each of five valves independently so that the percussion and vibration therapy delivered to the patient 36 may be tailored to specific needs based on inputs from a user through the user interface 139.

In operation, each conduit 232, 234, 236, 238, 240 is associated with a respective valve that is openable to allow air to flow into the respective chambers 222, 224, 226, 228, and 230. Each chamber 222, 224, 226, 228, and 230 is vented to atmosphere such that a burst of air into a chamber 222, 224, 226, 228, and 230 will expand the chamber 222, 224, 226, 228, or 230. The vents of the chambers 222, 224, 226, 228, and 230 are sized to constrict flow through the 222, 224, 226, 228, or 230 so that the chamber 222, 224, 226, 228, or 230 is rapidly expanded, thereby imparting a force onto the upper body of the patient 36. After the rapid expansion, closing of the respective valve causes the respective chambers to deflate back to the deflated state shown in FIG. 9. The chambers 224 and 228 are shown in an expanded state in FIG. 9. This continued expansion and deflation of the chambers 222, 224, 226, 228, and 230 provides the percussive or vibrational therapy to the patient 36. The action of the percussion and vibration system of the patient support apparatus 210 is similar to that disclosed in U.S. Pat. No. 6,119,291, entitled "PERCUSSION AND VIBRATION THERAPY APPARATUS, which is incorporated in its entirety be reference herein.

Figure 11:
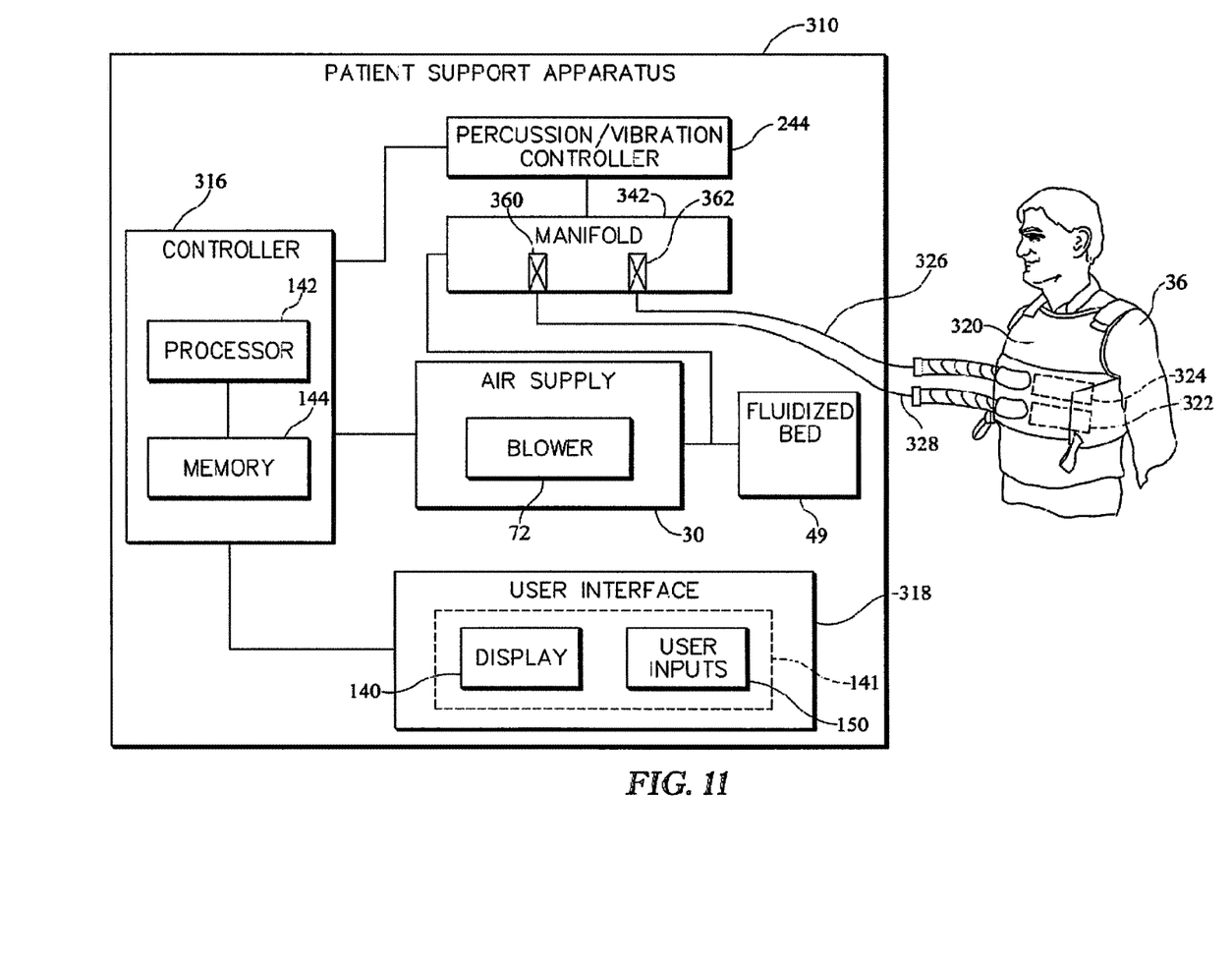
FIG. 11 is a partially diagrammatic view of another embodiment of a patient support apparatus that includes first section that includes an air fluidized therapy bed and further includes a garment that is operable to deliver high frequency chest wall oscillation (HFCWO) to a patient, the garment receiving pressurized air from an air supply that also provides pressurized air to the air fluidized therapy bed.

In still yet another embodiment shown in FIG. 11, high frequency chest wall oscillation (HFCWO) therapy is delivered to a patient 36 supported on or adjacent to a patient support apparatus 310 through a garment 320 that is worn by the patient 36. The garment 320 includes chambers 322 and 324 that are inflatable similar to the chambers 222, 224, 226, 228, and 230 discussed above with reference to the patient support apparatus 210. The patient support apparatus 310 includes the percussion/vibration controller 244 and a manifold 342 that includes two valves 360 and 362 to control the flow of air through two conduits 326 and 328 to provide air pulses to the chambers 322 and 324 of the garment 320. A controller 316, similar to controller 246 but programmed to control the HFCWO therapy of the patient support apparatus 310 allows a user to utilize a user interface 318 to control the operation of the HFCWO therapy of the patient support apparatus 310.

The garment 320 causes high frequency chest wall oscillation of the patient, which is known to help with relieving pulmonary congestion, such as that experienced by those who suffer from cystic fibrosis. In some embodiments, the garment 320 and the percussion/vibration controller 244 function similarly to the apparatus disclosed in U.S. Patent Application Publication No. 2011/0087143, entitled "THREE-DIMENSIONAL LAYER FOR A GARMENT OF A HFCWO SYSTEM" which is incorporated by reference herein in its entirety.

Figure 12:
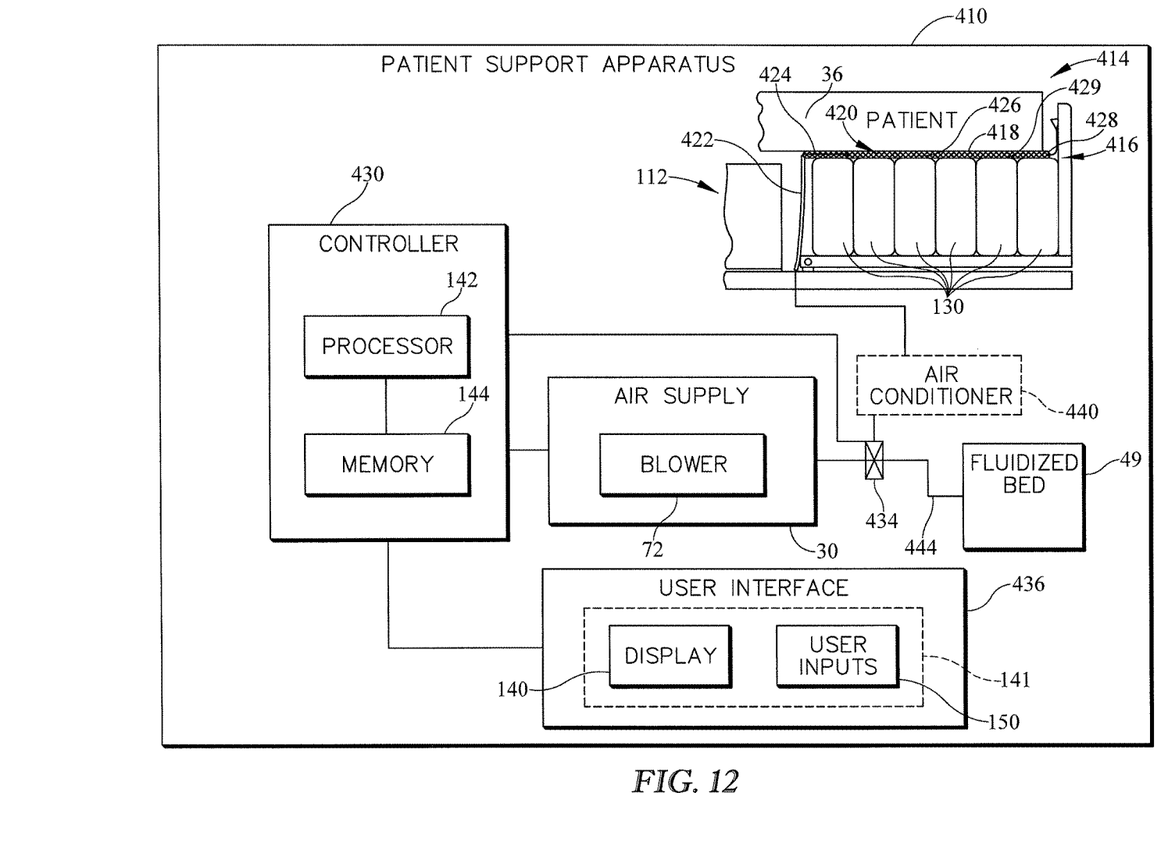
FIG. 12 is a partially diagrammatic view of another embodiment of a patient support apparatus including a side view a second portion of the patient support apparatus that includes a first portion that includes an air fluidized therapy bed, the second portion further including a micro-climate assembly supported on a set of bladders of the second portion.

In yet another embodiment, shown in FIG. 12, a patient support apparatus 410 includes a second portion 414 that includes the bladders 130, but further includes a micro-climate management assembly 416 which is positioned on top of the bladders 130 and operable to assist in the cooling and removal of moisture from the upper body of a patient 36 supported on the patient support apparatus 410.

The micro-climate management assembly 416 includes an upper layer 418 that comprises a urethane coated nylon ticking material that is air impermeable but vapor permeable. The upper layer 418 permits moisture, such as sweat, to permeate into an interior space 420 which includes a second layer 426 that comprises a three-dimensional spacer material that is sufficiently porous to permit air to flow therethrough. As air is introduced, under pressure, to an inlet 422 of the micro-climate management assembly 416, the air is urged through the second layer 426 in the direction of an arrow 424. The air flows through the second layer and moves moisture that has collected in the interior space 420 through the second layer 426 an urges the air and moisture out of an outlet 428. This action tends to cool the patient's skin and remove excess moisture, thereby reducing the potential for skin injury. A third layer 429 is coupled to the upper layer 418 to enclose the interior space 420.

The inlet 422 also comprises urethane coated nylon ticking material that is air impermeable but vapor permeable and is positioned between the bladders 130 and the first portion 112 of the patient support apparatus 410. The inlet 422 is a pliable material and is not prone to pinching or reduced flow due to mechanical interferences.

The flow to the micro-climate management assembly 416 is controlled by a controller 430 as shown in FIG. 12. The micro-climate management assembly 416 includes a diverter valve 434 that is positioned in a conduit 444 that conveys air from the air supply 30 to the inlet 49 of the first portion 112. Based on inputs from a user to a user interface 436, the diverter valve 434 may be engaged to divert a portion of the air flow from the air supply 30 to the micro-climate management assembly 416. In some embodiments, the patient support apparatus 410 may further include an air conditioner 440, shown in broken lines in FIG. 15, to condition the air from the air supply 30 to change the temperature or to remove fluid from the air. Conditioning of the air assists with reducing the temperature of the surface.

Further disclosure of a micro-climate assembly may be found in U.S. Application No. PCT/US09/40661, filed Apr. 15, 2009 and entitled MICROCLIMATE MANAGEMENT SYSTEM which is incorporated in its entirety by reference herein.

Although certain illustrative embodiments have been described in detail above, variations and modifications exist within the scope and spirit of this disclosure as described and as defined in the following claims.

The invention claimed is:

1. A patient support apparatus comprising
a controller,
a user interface,
a single air supply,
a first flow path pneumatically connecting the single air supply to the first patient support zone,
a diverter valve positioned in the first flow path,
a second flow path pneumatically connecting the diverter valve and a second patient support zone,
the first patient support zone comprising an air fluidization therapy bed including a fluidization space and a fluidizable medium positioned in the fluidization space, the air fluidization therapy bed receiving the a flow of pressurized air from the air supply, the flow of pressurized air operable to fluidize the fluidizable medium, and the second patient support zone comprising a micro-climate assembly, wherein the controller is operable, based on inputs to the user interface, to control the diverter valve to selectively divert a portion of the flow from the first flow path to the second patient support zone such that, when the diverter valve is engaged to divert a portion of fluid flow from the first flow path to the second patient support zone, the single air supply continuously supplies both the air fluidization therapy bed and the micro-climate assembly.

2. The patient support apparatus of claim 1, wherein the micro-climate assembly comprises an upper layer of vapor permeable material, a lower layer coupled to the upper layer to define a chamber having an inlet and an outlet, the chamber having an interior space, a three dimensional material positioned in the interior space, the second flow of air entering the chamber through the inlet and exiting the chamber through the outlet.

3. The patient support apparatus of claim 2, wherein patient support apparatus includes a first conduit from the air supply to the air fluidization therapy bed.

4. The patient support apparatus of claim 2, wherein the second flow is conditioned.

5. The patient support apparatus of claim 4, wherein the single air supply comprises a variable speed blower.

6. The patient support apparatus of claim 5, wherein the micro-climate assembly includes an outlet and the second flow is continuously exhausted through the outlet.

7. The patient support apparatus of claim 6, wherein air fluidized therapy bed includes a filter sheet and the first flow is continuously exhausted through the filter sheet.

8. The patient support apparatus of claim 1, wherein the single air supply comprises a variable speed blower.

9. The patient support apparatus of claim 8, wherein the micro-climate assembly includes an outlet and the second flow is continuously exhausted through the outlet.

10. The patient support apparatus of claim 9, wherein air fluidized therapy bed includes a filter sheet and the first flow is continuously exhausted through the filter sheet.

11. A patient support apparatus comprising
a controller,
a user interface,
a single air supply configured to continuously and simultaneously supply a first flow of air to a first patient support zone and a second flow of air to a second patient support zone,
a diverter valve coupled to the single air supply, the diverter valve being under control of the controller and the controller being responsive to user inputs at the user interface to operate the diverter valve, wherein the first patient support zone comprises an air fluidization therapy bed including a fluidization space and a fluidizable medium positioned in the fluidization space, the air fluidization therapy bed receiving a first flow of pressurized air from the air supply through the diverter valve, the first flow of pressurized air operable to fluidize the fluidizable medium, and wherein the second patient support zone comprises (i) a plurality of inflatable support bladders, and (ii) a micro-climate assembly supported on the support bladders, the micro-climate assembly including an upper layer of vapor permeable material, a lower layer coupled to the upper layer to define a chamber having an inlet and an outlet, the chamber having an interior space, a three dimensional material positioned in the interior space, the micro-climate assembly coupled to the diverter valve to selectively receive the second flow of air therefrom, the second flow of air entering the chamber through the inlet and exiting the chamber through the outlet, wherein the continuous and simultaneous first flow and second flow are at different rates and wherein the diverter valve is selectively engageable control the flow to the micro-climate assembly.

12. The patient support apparatus of claim 11, wherein the patient support apparatus further comprises a first conduit coupled to the diverter valve and a second conduit coupled to the diverter valve, the second conduit coupled to the micro-climate assembly.

13. The patient support apparatus of claim 12, wherein the second flow is conditioned.

14. The patient support apparatus of claim 13, wherein the single air supply comprises a variable speed blower.

15. The patient support apparatus of claim 14, wherein the second flow is continuously exhausted through the outlet of the micro-climate assembly.

16. The patient support apparatus of claim 15, wherein air fluidized therapy bed includes a filter sheet and the first flow is continuously exhausted through the filter sheet.

17. The patient support apparatus of claim 11, wherein the single air supply comprises a variable speed blower.

18. The patient support apparatus of claim 17, wherein the second flow is continuously exhausted through the outlet of the micro-climate assembly.

19. The patient support apparatus of claim 18, wherein air fluidized therapy bed includes a filter sheet and the first flow is continuously exhausted through the filter sheet.

20. The patient support apparatus of claim 19, wherein the second flow is conditioned.

* * * * *